United States Patent
Leonardi et al.

[11] Patent Number: 5,912,351
[45] Date of Patent: *Jun. 15, 1999

[54] ANHYDROUS 1,4-DIHYDROPYRIDINES AND SALTS THEREOF

[75] Inventors: Amedeo Leonardi, Milan; Gianni Motta, Barlassina, both of Italy

[73] Assignee: Recordati, S.A. Chemical and Pharmaceutical Company, Chiasso, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/645,963

[22] Filed: May 10, 1996

[30] Foreign Application Priority Data

May 12, 1995 [IT] Italy .................. MI95 A 0957
Jun. 14, 1995 [IT] Italy .................. MI95 A 1513

[51] Int. Cl.$^6$ .................. C07D 211/86
[52] U.S. Cl. .................. 546/321; 514/356
[58] Field of Search .................. 546/321

[56] References Cited

PUBLICATIONS

Sing et al. Tetrahedron 45, No. 12, 3967–74, Abstract, 1989.
Fox et asl. Physics and Chemistry of the Organic Solid State, Interscience Publishers, 1963.
Evans, An Introduction to Crystal Chemistry pp. 393–397, 1964.
Remington's Pharmaceutical Sciences 15th edition Mack Publising Company, 1975.
Berge et al. Journal of Pharceutical Sciences vol. 66, No. 1, 1977.
Pauletto et al., *J. Cardiov. Pharmacol.*, 19:2 (1992), S8–S16.
Sinzinger et al., *J. Cardiov. Pharmacol.*, 19:3 (1992), S29–S31.
Knorr et al., *Cardiovasc. Drugs Ther.*, 4:S5 (1990), 1027–1031.
Fleckenstein–Grün et al., *J. Human Hypertens.*, 6:S1 (1992), S13–S18.
Leslie et al., *Acta Anaesthesiol. Scand*, 37:S99 (1993), 33–37.
Borchard, *J. Cardiov. Pharmacol.*, 24:2 (1994), S85–S91.
Pauletto et al., *Drugs*, 48:S1 (1994), 1–7.
Gaviraghi et al., *Pharmacol. Res.*, 31:314 (1995), 251–254.
Nayler, *Am. J. Hypertens.*, 7:10(2) (1994), 126S–130S.
Weinstein, *J. Cardiov. Pharmacol.*, 12:6 (1988) S29–S35.
Henry, *Clin. Invest. Med.*, 10:6 (1987) 601–605.
Weinstein, *Am. J. Med.*, 86:S4(A) (1989) 27–32.

*Primary Examiner*—Jane Fan
*Attorney, Agent, or Firm*—Darby & Darby

[57] ABSTRACT

The subject invention provides anhydrous 1,4-dihydropyridines and salts thereof, and a method for preparing them. The 1,4-dihydropyridines have Formula I:

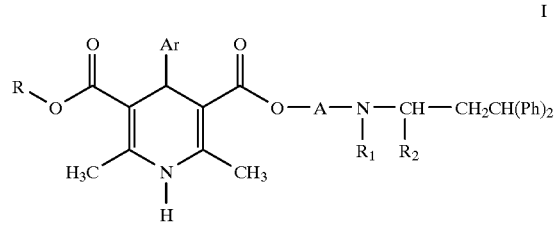

wherein:
  Ph is phenyl,
  Ar is: 2-nitrophenyl, 3-nitrophenyl, 2,3-dichlorophenyl or benzofurazan-4-yl,
  A is a branched chain alkylene radical having from 2 to 6 carbon atoms,
  R is a straight or branched chain alkyl radical having from 1 to 6 carbon atoms, optionally mono-substituted by an alkoxy substituent having from 1 to 6 carbon atoms,
  $R_1$ is hydrogen, hydroxy, or an alkyl radical having from 1 to 4 carbon atoms, and
  $R_2$ is hydrogen, or methyl.

9 Claims, 6 Drawing Sheets

ANHYDROUS 1,4-DIHYDROPYRIDINES AND SALTS THEREOF

FIELD OF THE INVENTION

The present invention relates to the use of 1,4-dihydropyridines to counter several processes which affect the development of atherosclerotic vascular lesions, such as, for example, myocyte proliferation and migration, cholesterol metabolism in macrophages and oxidative modification of low-density lipoproteins (LDL). Beneficial effects on the above biological processes are the basis for prevention of atherosclerotic degradation in arterial walls of humans. Another aspect of the invention relates to particular forms of, and compositions containing, such compounds and adapted for this therapeutic use.

BACKGROUND OF THE INVENTION

The compounds of the invention are known for their coronary dilating and antihypertensive activity from U.S. Pat. No. 4,705,797. However, the anhydrous form of such compounds is novel and forms part of the present invention.

A particularly preferred compound is methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate (lercanidipine), and pharmaceutically acceptable salts thereof. These compounds can be prepared according to the methods cited in U.S. Pat. No. 4,705,797 or the methods disclosed herein.

Also, particularly preferred are the resolved enantiomers of lercanidipine. The preparation of the individual enantiomers is described in the present specification.

Arteriosclerosis, a generic term for thickening and hardening of the arterial wall, is responsible for many deaths in the United States and other westernized societies. One type of arteriosclerosis is atherosclerosis, a disorder of the larger arteries that underlies most coronary artery disease, aortic aneurysm, and arterial disease of the lower extremities. Atherosclerosis plays a major role in cerebrovascular disease and is a leading cause of death in the United States, both above and below age 65 (E. L. Bierman in *Harrison's Principles of Internal Medicine XII* Ed., page 992 (1991)).

It is now recognized that atherosclerosis is a multifactorial process that, when leading to clinical sequelae, is based on extensive proliferation of migrated smooth muscle cells (myocytes) within the intima of the affected artery. The atherosclerotic plaque formation is believed to be the result of three fundamental biological processes. These are:

1) migration and proliferation of intimal smooth muscle cells, together with variable numbers of accumulated macrophages and T-lymphocytes;
2) formation by the proliferated smooth muscle cells of large amounts of connective tissue matrix, including collagen, elastic fibers, and proteoglycans; and
3) accumulation of lipid, principally in the form of cholesterol esters and free cholesterol within the cells as well as in the surrounding connective tissues.

(R. Ross et al., *Science*, 180: 1332 (1973); R. Ross et al., *N. Eng. J. Med.*, 295: 369 (1976); R. W. Wissler et al., *Prog. Cardiovasc. Dis.*, 18: 341 (1976)).

In addition, a number of experimental reports ascribe a key role to the oxidative modification of low density lipoproteins (LDL) in the early stages of atherosclerosis in humans, where hypercholesterolemia represents the major risk factor associated with the increased incidence of the disease. Available data has lead to the belief that LDL can undergo oxidative modification (D. Steinberg et al., *N. Eng. J. Med.*, 320: 915 (1989); J. L. Witztum, *Lancet*, 344: 793 (1994)) and that oxidized LDL has been shown to promote atherogenesis by a number of mechanisms, including enhanced uptake of LDL in tissue macrophages which leads to lipid accumulation and chemotactic activity for monocytes (M. S. Brown et al., *Ann. Rev. Biochem.*, 52: 223 (1983)), and cytotoxicity to arterial wall endothelial cells (S. Parthasarathy et al., *Prog. Lipid Res.*, 31: 127 (1992)).

SUMMARY OF THE INVENTION

It has now been found that 1,4-dihydropyridines, such as lercanidipine and each enantiomer of lercanidipine are able to counteract many of the biological processes leading to atherosclerotic lesions. Therefore, these compounds are useful in a mammal, including a human in need of such treatment to prevent, retard, or reduce the atherosclerotic degradation of the arterial wall, hypercholesterolemia and the various diseases caused by these, such as, for example, ischemic heart diseases such as myocardial infarction and cerebrovascular diseases such as cerebral infarction and cerebral apoplexy.

The compounds of the invention are also useful for the inhibition of restenosis following percutaneous transluminal coronary angioplasty (PTCA) and for suppressing the progression of vascular hypertrophy associated with hypertension.

The subject invention provides a method for preventing, retarding, and/or reducing atherosclerotic lesions and preventing atherosclerotic degradation of arterial walls. The method comprises administration of an effective amount of a compound having Formula I:

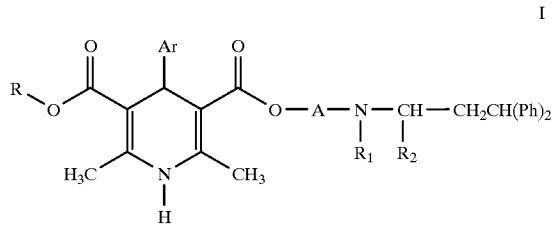

wherein:
Ph is phenyl,
Ar is: 2-nitrophenyl, 3-nitrophenyl, 2,3-dichlorophenyl or 5 benzofurazan-4-yl,
A is a branched chain alkylene radical having from 2 to 6 carbon atoms,
R is a straight or branched chain alkyl radical having from 1 to 6 carbon atoms, optionally mono-substituted by an alkoxy substituent having from 1 to 6 carbon atoms,
$R_1$ is hydrogen, hydroxy, or an alkyl radical having from 1 to 4 carbon atoms, and
$R_2$ is hydrogen, or methyl.

Also useful in the present invention are resolved enantiomers of the compounds having formula 1, pharmaceutically acceptable acid addition salts, and hydrated or solvated forms of any of these compounds.

The present invention also contemplates unit dosage forms that include an effective amount of at least one of the (R)-enantiomer, the (S)-enantiomer, or the racemate of the compounds of the invention.

It has been discovered that the compounds of the invention can be prepared in anhydrous (unsolvated) form by recrystallizing the compound in an aprotic solvent and a protic solvent. In the recrystallization either aprotic or protic solvent can be used prior to the other. The anhydrous compounds formed have improved stability when compared to the hydrated or solvated compounds. Particularly preferred among these 1,4-dihydropyridine derivatives are lercanidipine, its enantiomers, and pharmaceutically acceptable salts thereof. Lercanidipine is methyl 1,1-N-trimethyl-N-(3,3-diphenylpropyl)-2-aminoethyl 1,4-dihydro-2,6-dimethyl-4-(3-nitrophenyl)-pyridine-3,5-dicarboxylate.

The (S)-enantiomer and the racemate of lercanidipine, both possess antihypertensive activity, and can be used for patients in need of treatment for both hypertension and diseases related to atherosclerotic phenomena.

On the other hand, (R)-lercanidipine, having only minimal antihypertensive activity, has substantial activity in, and can be used for treating conditions involving, smooth muscle cell migration and proliferation and diseases related to atherosclerotic phenomena without any concomitant cardiovascular effect. This enantiomer is useful for treatment of patients for whom reduction of blood pressure would be undesirable.

The invention also provides for the preparation of a composition useful for the treatment, i.e., the prevention, arrest, retardation, or at least partial reversal of atherosclerotic degradation in the arterial walls of a patient in need of said treatment using a compound of the general formula I.

DETAILED DESCRIPTION OF THE INVENTION

Figure 1:
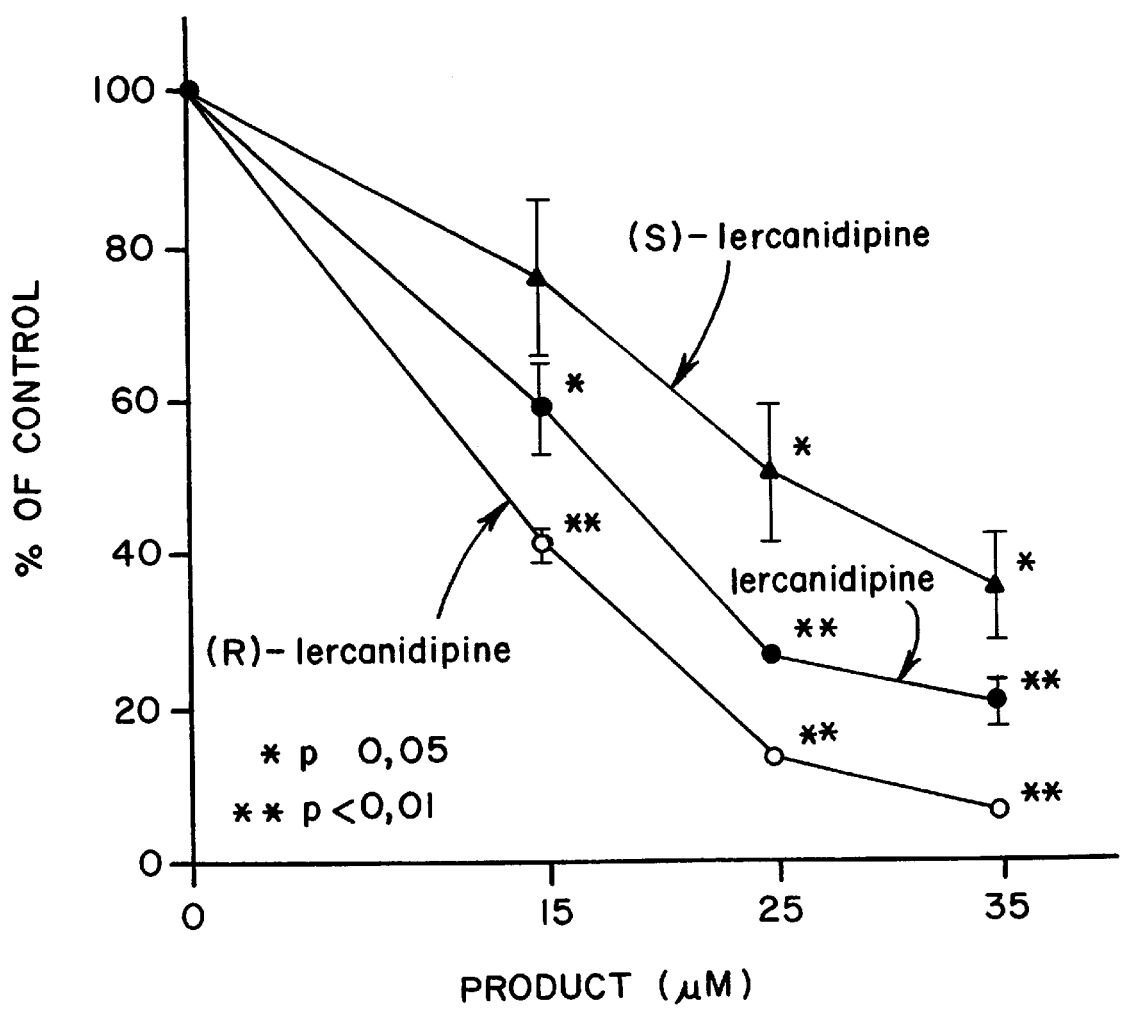
FIG. 1 is a graphical representation of the effect of lercanidipine and its enantiomers on [$^3$H]-thymidine incorporation into myocytes of rat smooth muscle cells.

All patents, patent applications, and literature references cited in the specification are hereby incorporated by reference in their entirety. In the case of inconsistencies, the present disclosure, including definitions, will prevail. "Treatment" of atherosclerosis is intended to include preventing, retarding, and/or reducing atherosclerotic lesions and preventing, retarding, and/or reducing atherosclerotic degradation of arterial walls, in mammals, particularly humans. In particular, the inhibition or counteracting of the following processes, which lead to atherosclerotic lesions, can be considered very useful for the treatment of atherosclerosis. They are:

1) migration and proliferation of intimal smooth muscle cells, together with variable numbers of accumulated macrophages and T-lymphocytes;
2) formation by the proliferated smooth muscle cells of large amounts of connective tissue matrix, including collagen, elastic fibers, and proteoglycans; and
3) accumulation of lipid, principally in the form of cholesteryl esters and free cholesterol within the cells as well as in the surrounding connective tissues.

According to the present invention, treatment constitutes any improvement in one or more clinical or histological symptoms or diagnostic markers observed by the attending physician or determined by quantitative or semiquantitative techniques. Non-limiting examples include techniques such as, analysis of blood, ultrasound and other imaging techniques such as angiography. Several of these techniques have been developed and are well-known. Patients who are likely to require this treatment are those suffering from or at risk for myocardial infarct, stroke, hyperlipidemia, or hypertension.

Lercanidipine can be prepared by Hantzsch cyclization of methyl 3-aminocrotonate (1) with 1,1,N-trimethyl-N-(3,3-diphenylpropyl)-2-aminoethyl α-acetyl-3-nitrocinnamate (2) (Scheme 1), according to the method described in U.S. Pat. No. 4,705,797.

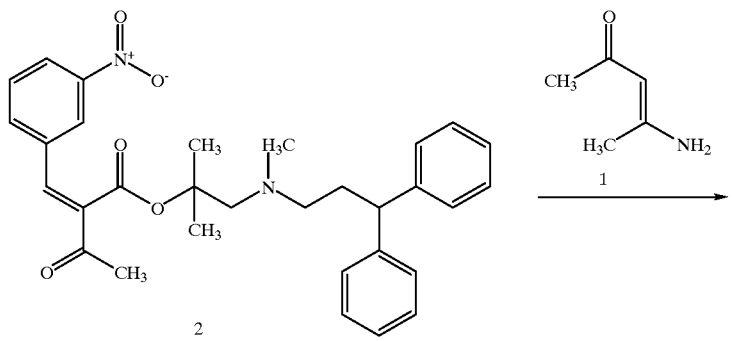

SCHEME 1

-continued

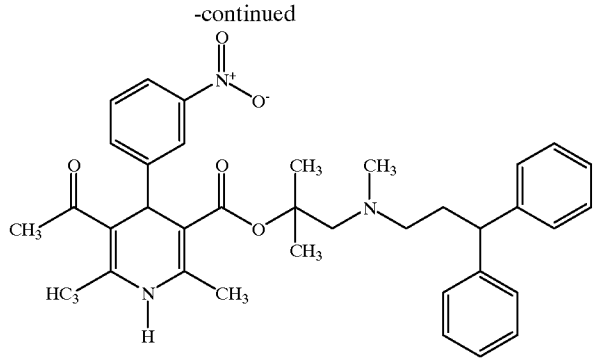

LERCANIDIPINE

However, the cyclisation method described in the U.S. Pat. No. 4,705,797 leads to several impurities and consequently a low yield of the product is obtained. The removal of the reaction byproducts requires the use of purification techniques, e.g., column chromatography, which are difficult to apply on an industrial scale.

Alternatively, lercanidipine can be prepared by esterification of 1,4-dihydro-2,6-dimethyl-5-methoxycarbonyl-4-(3-nitrophenyl)pyridine-3-carboxylic acid (3) with 2,N-dimethyl-N-(3,3-diphenylpropyl)-1-amino-2-propanol (4) (Scheme 2) according to the method described in Example 3.

Resolved lercanidipine enantiomers can be obtained by the esterification method illustrated in Scheme 2 using the corresponding homochiral acids which, when present in 1:1 ratio, constitute the above cited racemic acid 3.

The homochiral acids, hereinbelow called for convenience, acid 5 (the (R)-enantiomer) and acid 6 (the (S)-enantiomer), can be conveniently prepared by resolution of racemic acid 3 according to the method reported by A. Ashimori et al., *Chem. Pharm. Bull.* 39: 108 (1991).

The esterification reaction can be performed in the presence of a coupling agent (e.g.: dicyclohexylcarbodiimide, N,N'-carbonyldiimidazole or diethyl cyanophosphonate),

SCHEME 2

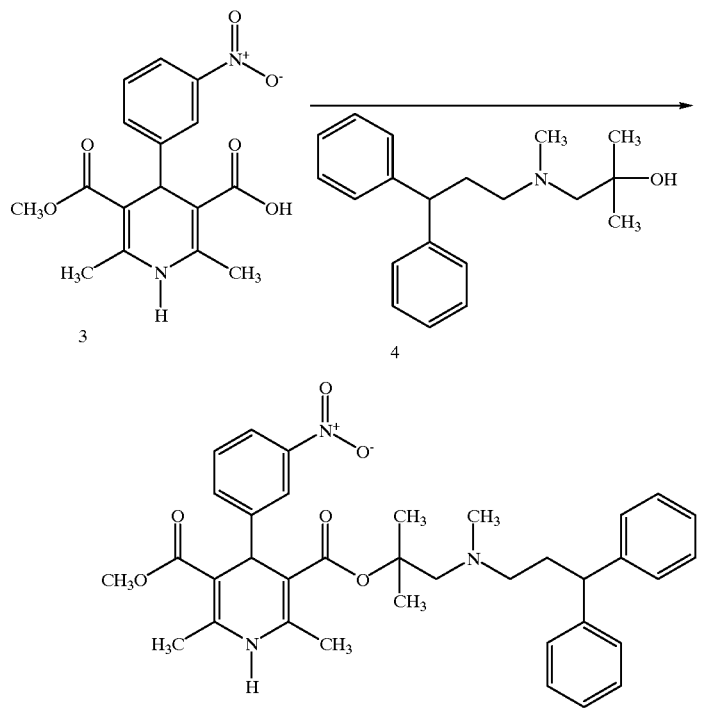

LERCANIDIPINE optionally in the presence of a promoting agent (e.g.: N-hydroxysuccinimide or 4-dimethylaminopyridine) in aprotic or chlorinated solvents (e.g.: N,N-dimethylformamide or chloroform) at temperatures ranging from −10 to 140° C. according to well-known synthetic methods: Albertson, *Org. React.* Vol. 12, 205–212 (1962); Doherty et al., *J. Med. Chem.* 35: 2 (1992); Ishihara, *Chem. Pharm. Bull.* 39: 3238 (1991).

Alternatively, lercanidipine enantiomers can be prepared by reacting acid 5 (or acid 6) with alkyl chloroformate in presence of a tertiary amine (e.g., triethylamine), then adding the intermediate alcohol (4) at about 0–80° C. Optionally, a promoting agent (e.g., 1-hydroxypiperidine) may be added before the addition of the intermediate (4) (Albertson, *Org. React.* Vol. 12, 157 (1962)).

The compounds and enantiomers of the invention can also be prepared by conversion of acid 5 (or acid 6) into the corresponding acyl halide using inorganic acid halides (e.g.: phosphorous pentachloride, oxalyl chloride, phosphorous trichloride, phosphorous oxychloride, or thionyl chloride) in a chlorinated solvent (e.g.: chloroform, dichloroethane, dichloromethane, 1,1,1-trichloroethane and the like), optionally in the presence of promoting agents (e.g.: N,N-dimethylformamide) at temperature ranging from about −10 to about 85° C. The resolved acyl halides can optionally, but need not, be isolated before the addition of the intermediate alcohol (4).

The lercanidipine enantiomers thus obtained are purified according to methods known in the art, either as a free base (e.g.: by column chromatography) or as a salt (e.g.: by reprecipitation or recrystallization). The above methods can also be used for all compounds having formula I.

It has been discovered that racemic mixtures of the compounds of the invention purified by recrystallization can be prepared in anhydrous or unsolvated form by recrystallizing the compound from a solution of the compound in; (i) an aprotic solvent; and (ii) a protic solvent. The anhydrous compounds have improved stability and lower hygroscopicity when compared to the hydrated/solvated compounds.

The lercanidipine can be obtained by esterification from the corresponding dihydropyridine acid in accordance with a one-step reaction process starting with the acid chloride of compound 3, prepared in situ. This route provides improved yields and the formation of fewer reaction byproducts. The improved purity of the compounds of the invention avoids the use of chromatographic columns to isolate the desired final product. The compounds can be obtained directly by crystallisation as the hydrochloride salt with a high degree of purity.

The lercanidipine hydrochloride can be prepared according to the present invention in the anhydrous crystalline form, melting within a two degree range from about 185 to 190° C. range after recrystallisation of the crude hydrochloride compound from a solution of the compound in; (i) an aprotic solvent; and (ii) a protic solvent.

Examples of aprotic solvents include chlorinated solvents, such as, for example, chloroform, dichloromethane, dichloroethane, chlorobenzene, 1,1,1-trichloroethane, and the like; non-chlorinated solvents, such as, for example, ethyl acetate, methyl acetate, tetrahydrofuran, dioxane, N,N-dimethyl-formamide, dimethylcarbonate, toluene, xylene, an ($C_5$–$C_7$) alkane, a ($C_5$–$C_7$) cycloalkane and the like.

Examples of protic solvents include solvents, such as, for example, methanol, ethanol, propanol, isopropanol, n-butanol, sec-butanol, tert-butanol and the like. All solvents can be used alone or optionally in a mixture with other solvents. All water miscible solvents can be used alone or in a mixture which may comprise at least one solvent and optionally include water.

Pharmaceutically acceptable salts are prepared from the free bases in a conventional manner.

Preferred pharmaceutically acceptable acid addition salts are those such as, for example, hydrochloric, sulfuric, maleic, succinic, citric, methanesulfonic and toluenesulfonic acids, and the like.

The hydrated and solvated forms of the compounds of the invention include compounds which have water or solvent molecules associated with them. There can be as little as about 0.25 molecules of water or solvent or there can be several water or solvent molecules for each lercanidipine molecule.

Typical solvents which associate or solvate the lercanidipines are solvents which can be used for recrystallization. Examples of these solvents include water, alcohols such as, for example, methanol, ethanol, propanol, isopropanol, n-butanol, sec-butanol, tert-butanol and the like.

According to the invention, the 1,4-dihydropyridine derivative having formula I may be administered to the patient as such, or in the form of any of its pharmaceutically acceptable salts, hydrates or solvates. It has been determined that the bioavailability and efficacy of the compounds having formula I is comparable whether administered in the anhydrous form or in a hydrated or solvated form.

Preferred pharmaceutically acceptable acid addition salts include those formed with hydrochloric, sulfuric, maleic, succinic, citric, methanesulphonic and toluenesulphonic acids; they may be prepared from the free bases in conventional manner. Whatever the form (base, salt, hydrate or solvate), the active ingredient will usually be administered in admixture with a pharmaceutically acceptable carrier.

For the purpose of oral therapeutic administration, the active compounds of the invention can be incorporated with excipients and used in the form of tablets, troches, capsules, elixirs, suspensions, syrups, wafers, chewing gum, and the like.

These preparations will typically contain at least about 0.5% of active compounds, but the amount of active ingredient can be varied depending upon the particular form and may conveniently contain from about 5% to about 70% of the weight of the unit. The amount of active compound in such compositions is such that a suitable dosage will be obtained. However, the desired dosage can be obtained by administering a plurality of dosage forms.

The compounds of the invention can be administered as an oral dosage of from about 0.1 to about 400 mg, preferably from about 1 to about 200 mg, and most preferably from about 5 to about 100 mg, per subject treated, per day. Therapy can continue for several months or years or indefinitely.

Preferred compositions and preparations according to the invention are prepared so that an oral dosage unit form contains from about 0.1 to about 400 mg of active compound.

The tablets, pills, capsules, troches, and the like can also contain, for example, the following optional ingredients: a binder such as, for example, microcrystalline cellulose, tragacanth gum, gelatin, and the like; an excipient such as, for example, starch or lactose, a disintegrating agent such as, for example, alginic acid, sodium starch glycolate, corn starch, and the like; a lubricant such as, for example, magnesium stearate or hydrogenated castor oil, a glidant such as, for example, colloidal silicon dioxide. Sweetening agents such as, for example, sucrose or saccharin or flavoring agents such as, for example, peppermint, methyl salicylate, or orange flavoring can also be added.

The active compounds of the invention can be orally administered, for example, with an inert diluent or with an edible carrier. They can, for example, be enclosed in gelatin capsules, or they can be compressed into tablets.

When the dosage unit form is a capsule, it can contain, in addition to materials described above, a liquid carrier such as, for example, a fatty oil.

For the purpose of parenteral administration, the 1,4-dihydropyridine derivatives may be incorporated into a solution or suspension.

These preparations typically contain at least 0.1% of active compound, but the amount of active ingredient may vary between 0.5% and about 30% of the weight thereof. The amount of active compound in such compositions is such that a suitable dosage will be obtained.

Preferably a parenteral dosage unit contains between 0.5 to 100 mg of active compound. The solutions or suspensions may also include the following components: a sterile diluent such as water for injection, saline solution, fixed oils, polyethylene glycols, glycerine, propylene glycol or other synthetic solvents; an antibacterial agent such as benzyl alcohol or methyl parabens; an antioxidant such as ascorbic acid or sodium bisulfite; a chelating agents such as ethylenediaminetetraacetic acid; a buffer such as an acetate, a citrate or a phosphate and an agent for the adjustment of tonicity such as sodium chloride or dextrose. Parenteral multiple dose vials may be of glass or plastics material.

The parenteral multiple dose vials can be of glass or plastic materials.

Other dosage unit forms can contain various other materials which modify the physical form of the dosage unit, for example, coatings. Thus, tablets or pills can be coated with a sugar, shellac, or another enteric coating agent.

A syrup can contain, in addition to the active compounds, sucrose as a sweetening agent, preservatives, dyes, colorings, and flavorants.

For the purpose of parenteral therapeutic administration, the active compounds of the invention can be incorporated into a physiologically acceptable solution or suspension.

These preparations preferably contain at least about 0.1% of active compound, but may be varied to from about 0.5% to about 30% by weight thereof. The amount of active compound in these compositions is such that a suitable dosage of from about 5 to about 100 mg will be obtained upon administration of the solution or suspension.

Preferred compositions and preparations according to the present inventions are prepared so that a parenteral dosage unit contains from about 5 to about 100 mg of active compound.

The solutions or suspensions can also include the following components: a sterile diluent such as, for example, water for injection, saline solution, fixed oils, polyethylene glycols, glycerine, propylene glycol, other synthetic solvents, and the like; antibacterial agents such as, for example, benzyl alcohol, methyl parabens, and the like; antioxidants such as, for example, ascorbic acid, sodium bisulfite, and the like; chelating agents such as, for example, ethylenediaminetetraacetic acid and the like; buffers such as, for example, acetates; citrates, phosphates, and the like, and agents for the adjustment of tonicity such as, for example, sodium chloride, dextrose, and the like.

Materials used in preparing these various compositions for practicing the invention should be pharmaceutically pure and non-toxic at the level employed.

Additional compositions suitable for administration by various routes and containing compounds according to the present invention are also within the scope of the invention.

Dosage forms, additional ingredients and routes of administration contemplated herein include those disclosed in U.S. Pat. No. 4,089,969 and U.S. Pat. No. 5,091,182, both incorporated by reference in their entirety.

EXAMPLES

The following examples illustrate the invention without limitation.

Example 1

(S)-(+)-METHYL 1,1-N-TRIMETHYL-N-(3,3-DIPHENYLPROPYL)-2-AMINOETHYL 1,4-DIHYDRO-2,6-DIMETHYL-4-(3-NITROPHENYL)PYRIDINE-3,5-DICARBOXYLATE ((S)-LERCANIDIPINE) HYDROCHLORIDE•0.5 $H_2O$

Thionyl chloride, 0.13 ml, was added, at $-10°$ C., to a stirred suspension of 0.54 g of (R)-1,4-dihydro-2,6-dimethyl-4-(3-nitrophenyl)-5-methoxycarbonylpyridine-3-carboxylic acid in 2.9 ml of anhydrous dichloromethane and 0.75 ml of anhydrous N,N-dimethylformamide under a nitrogen atmosphere, and sheltered from the direct light.

After 1 hour at $0°$ C., a solution of 0.48 g of 2,N-dimethyl-N-(3,3-diphenyl-propyl)-1-amino-2-propanol, (prepared as described in U.S. Pat. No. 4,705,797), in 1 ml of dichloromethane, cooled to $-5°$ C., was added. After stirring for 3 hours at $0°$ C. and standing overnight at $20-25°$ C., the solvent was evaporated in vacuo and the residue was dissolved in 20 ml of ethyl acetate. The organic phase was washed sequentially, with brine (4 ml), 10% aqueous sodium carbonate solution (5×4 ml), brine (4 ml), 1 N hydrochloric acid (5×5 ml), brine (4 ml), 10% aqueous sodium carbonate solution (2×5 ml) and with brine (4 ml). The organic phase was dried over anhydrous sodium sulfate and evaporated to dryness in vacuo. The product was purified by flash chromatography on silica gel column eluting with petroleum ether-acetone 85:15. The individual, pure, TLC fractions (petroleum ether—acetone 7:3 by volume and chloroform—5 N methanolic ammonia 99:1.1 by volume) were combined and evaporated to provide a residue that was dissolved in 75 ml of diethyl ether containing 3% of acetone. After filtration the solution was acidified with 3 N ethereal hydrogen chloride and the precipitate was collected by suction filtration and dried at $78°$ C./15 mmHg to provide 0.66 g of the title compound.

M.P. $115-125°$ C.; $[\alpha]_D^{25}=+70.56°$ (MeOH; c=0.981).

Elemental analysis % for $C_{36}H_{41}N_3O_6$•HCl•0.5 $H_2O$ Found: C, 65.47; H, 6.57; N, 6.29; Cl, 5.32; $H_2O$, 1.68 Calc.: C, 65.79; H, 6.60; N, 6.39; Cl, 5.39; $H_2O$, 1.37

$^1$H-NMR Spectrum of the base at 200 MHz (CDCl$_3$, δ):
8.10 (m, 1H) nitrophenyl, CH in 2
7.97 (m, 1H) nitrophenyl, CH in 4
7.62 (m, 1H) nitrophenyl, CH in 6
7.33 (dd, 1H) nitrophenyl, CH in 5
7.29–7.10 (m, 10H) H benzhydryl aromatics
5.79 (bs, 1H) pyridine, NH
5.05 (s, 1H) pyridine, CH in 4
3.92 (t, 1H) benzhydryl, CH
3.63 (s, 3H) COOCH$_3$
2.57 (m, 2H) OC(CH$_3$)$_2$CH$_2$N
2.40–2.23 (m, 2H) N(CH$_3$)CH$_2$,CH$_2$
2.33/2.27 (2s, 6H) pyridine, CH$_3$ in pos. 2 and 6
2.19–2.09 (m, 2H) N(CH$_3$)CH$_2$CH$_2$
2.17 (s, 3H) NCH$_3$
1.35/1.31 (2s 6H) OC(CH$_3$)$_2$CH$_2$N Example 2

(R)-(−)METHYL 1,1-N-TRIMETHYL-N-(3,3-DIPHENYLPROPYL)-2-AMINOETHYL 1,4-DIHYDRO- 2,6-DIMETHYL-4-(3-NITROPHENYL)PYRIDINE-3,5-DICARBOXYLATE ((R)-LERCANIDIPINE) HYDROCHLORIDE•$H_2O$

The title compound was obtained by the method described in Example 1 for the (S)-enantiomer, starting with (S)-1,4-dihydro-2,6-dimethyl-4-(3-nitrophenyl)-5-methoxycarbonylpyridine-3-carboxylic acid.

M.p. 115–120° C., $[a]_D^{25}$=−70.88° (MeOH, c=0.975).

Elemental analysis % for $C_{36}H_{41}N_3O_6$•HCl•$H_2O$ Found: C, 64.93; H, 6.62; N, 6.24; Cl, 5.41; $H_2O$, 2.50 Calc.: C, 64.90; H, 6.60; N, 6.31; Cl, 5.32; $H_2O$, 2.70

The $^1$H-NMR spectrum of the base in $CDCl_3$ was identical to the $^1$H-NMR spectrum for the (S)-enantiomer from Example 1.

Example 3

METHYL 1,1-N-TRIMETHYL-N-(3,3-DIPHENYLPROPYL)-2-AMINOETHYL 1,4-DIHYDRO-2,6-DIMETHYL-4-(3-NITROPHENYL) PYRIDINE-3,5-DICARBOXYLATE (LERCANIDIPINE) HYDROCHLORIDE.

Thionyl chloride, 45.8 g (0.385 mole), was added dropwise over 15 minutes into a stirred mixture comprising 11 6.2g (0.35 mole) of 2,6-dimethyl-5-methoxycarbonyl-4-(3-nitrophenyl)-1,4-dihydropyridine-3-carboxylic acid (3) (prepared as described in German patent DE 2,847,237), 645 mL of anhydrous dichloromethane and 150 mL of anhydrous dimethylformamide, maintained under a nitrogen atmosphere at a temperature of −4 to +1° C. The mixture was stirred and maintained at this temperature for 1 hour. This was followed by dropwise addition of 104.1 g (0.35 mole) of 2,N-dimethyl-N-(3,3-diphenyl-propyl)-1-amino-2-propanol (4) (prepared as described in U.S. Pat. No. 4,705,797), dissolved in 105 mL of anhydrous dichloromethane, over 15 minutes at a temperature of −10 to 0° C. After stirring for 3 hours at 0° C. and standing overnight at room temperature, the solvent was evaporated under vacuum and the residue dissolved in 3500 mL of ethyl acetate. The organic solution was washed sequentially with: brine (700 mL), 10% aqueous sodium carbonate solution (5×700 mL), brine (700 mL), 1 N hydrochloric acid (5×700 mL) and finally with brine (700 mL). The organic layer was dried over anhydrous sodium sulphate for 30 minutes, filtered, shaken with 23 g of charcoal and filtered again. The solution volume was first reduced to about 1 liter by evaporation under vacuum, and the product allowed to crystallize. After standing 24 hours at 0 to 5° C., the crystalline product was collected by vacuum filtration and recrystallized from ETOH 99% to provide 179.5 g (78% yield) of the title compound. M.P. 186–188° C.

Example 4A

EFFECTS ON ARTERIAL MYOCYTE PROLIFERATION

Animal models of vascular injury have shown that an arterial lesion is followed by proliferation of medial myocytes, many of which migrate into the intima and further proliferate to form a neointimal lesion. The causes of these events are not completely understood. Recent findings have concluded that myocytes make up approximately 90–95% of the cellular population of the atherosclerotic lesion in young adults and compose an average of 50% of the advanced atherosclerotic plaque. In addition, vascular myocytes contribute to lesion formation and growth by synthesis of an extracellular matrix or they can accumulate lipids and become foam cells.

Thus, the elucidation of the factors affecting these phenomena affords new entry points for selective interference and inhibition of the process of atherogenesis (R. W. Wissler et al:, Am. J. Med. 91: (S1 B), 3S (1991); S. M. Schwartz et al., Circ. Res. 58: 427 (1986); A. W. Cloves et al., J. Cardiov. Pharmacol. 14: 512 (1989); R. W. Wissler et al., Ann. NY Acad. Sci. 598: 418 (1990).

Migration of myocytes was investigated for the present invention using rat aortic smooth muscle cells in the presence of fibrinogen as chemotactic factor, whereas for studies on their proliferation rat and human cells were used. Cell count and [3H]-thymidine incorporation were used to evaluate myocytes growth. The methodology was as follows:

Myocytes were cultured from the intima-medial layer of the aortas of male Sprague-Dawley rats (200–250 g). Cells were grown in monolayers at 37° C. in a humidified atmosphere of 5% $CO_2$ in Eagle's minimum essential medium supplemented with 10% (v/v) fetal calf serum, 100 U/ml penicillin, 0.1 mg/ml streptomycin, 20 mM tricine buffer and 1% (v/v) non-essential amino acid solution. The medium was changed every third day. Cells were used between the 4th and 10th passage. Cell viability was timely assessed by trypan blue exclusion. Myocytes were identified for growth behavior, morphology and using monoclonal antibody specific for a-actin, the actin isoform typical of myocytes. Human vascular myocytes (A 617 from human femoral artery) kindly provided by Prof. G. Gabbiani of The General Pathology Institute (Geneva University—Switzerland) were grown in the same culture conditions. (These or other human vascular myocytes can be obtained and cultured as described by Corsini et al., Atherosclerosis, 101: 117–125, (1993); Corsini et al., Pharm. Res, 23: 173 (1991); Ross, R, J. Cell Bio., 50: 172, (1971); and Skalli, 0. et al., J. Cell Bio., 103: 2787 (1986)).

Cells were seeded at various densities for rat ($2\times10^5$) and human (5 $10\times10^4$) myocytes/petri dish (35 mm), and incubated with Eagle's minimum essential medium supplemented with 10% fetal calf serum. Twenty-four hours later the medium was changed to one containing 0.4% fetal calf serum to stop cell growth, and the cultures were incubated for 72 hours. At this time (time 0) the medium was replaced by one containing 10% fetal calf serum in the presence or absence of known concentrations of the 1,4-dihydropyridine compounds being tested (shown in Table 1). The incubation was continued for an additional 72 hours at 37° C. Just before the addition of the test substances, an aliquot from each petri dish was used for cell counting. Cell proliferation was evaluated by cell count after trypsinization of the monolayers using a Coulter Counter model ZM. Cell viability was assessed by trypan blue exclusion, and found to be greater than 95% at the drug concentrations used.

TABLE 1

MYOCYTES GROWTH INHIBITION MEASURED BY CELL COUNT

| Myocytes from | LE $IC_{50}(\mu M)$ | (R)-LE $IC_{50}(\mu M)$ | (S)-LE $IC_{50}(\mu M)$ | NI $IC_{50}(\mu M)$ | LA $IC_{50}(\mu M)$ |
|---|---|---|---|---|---|
| SD Rat | 31.2 | 30.7 | 33.3 | 38.8 | 23.6 |
| SHR Rat | 14.1 | 9.2 | 16.8 | n.t. | n.t. |
| WK Rat | 16.4 | 15.3 | 20.7 | n.t. | n.t. |
| Human | 25.3 | n.t. | n.t. | n.t. | n.t. |

LE = Lercanidipine
NI = Nicardipine
LA = Lacidipine
$IC_{50}$ = concentration required to inhibit cell growth by 50%
SD = Sprague Dawley
SHR = Spontaneously Hypertensive
WK = Wistar Kyoto
n.t. = not tested The data from Table 1 show that compounds of the invention, particularly, racemic lercanidipine and its resolved enantiomers inhibited the rat and human myocyte proliferation in a concentration-dependent manner and showed practically the same activity as the reference 1,4-dihydropyridines tested (NI and LA).

It was found that lercanidipine (and its enantiomers) proved active on the cells from all the species investigated, in particular, humans.

Example 4B
EFFECTS ON ARTERIAL MYOCYTE PROLIFERATION

In another experiment, synchronization of myocytes to the $G_0/G_1$ interphase of the cell cycle was accomplished by incubating logarithmically growing cultures ($3 \times 10^5$ cells/plate) for 96–120 hours in a medium containing 0.4% fetal calf serum. Quiescent cells were incubated for 20 hours in a fresh medium with 10% fetal calf serum in the presence of the tested drugs. Cell proliferation was then estimated by nuclear incorporation of [$^3$H]thymidine, incubated with cells (1 $\mu$Ci/ml medium) for 2 hours. Radioactivity was measured with Filter-Count scintillation cocktail (AQUASOL® Scintillation cocktail available from Packard-Groningen, Netherlands).

The results, expressed as cell proliferation (as % of control) against amount of the compound of the invention (Lercanidipine and its enantiomers) tested, are shown in FIG. 1. The decrease in [$^3$H]-thymidine uptake of myocytes confirmed the high potency of the compounds of the invention in inhibiting cell proliferation.

Example 5
EFFECTS ON ARTERIAL MYOCYTE MIGRATION

Migration of rat myocytes was examined using a 48-well micro chemotaxis chamber (Neuro-Probe, USA). Freshly trypsinized myocytes prepared according to the procedure in Example 4A were suspended in a medium supplemented with 5% fetal calf serum (assay medium). The lower wells, containing 27 $\mu$l of the assay medium that included fibrinogen (600 $\mu$g/ml) as chemotactic agent, were covered with a polyvinylpyrrolidone-free polycarbonate filter (8 $\mu$M pore size). Fifty $\mu$l of the cell suspension ($1 \times 10^6$ cells/ml) were placed in the upper compartment with the tested compounds. Incubation was carried out for 5 hours at 37° C. in an atmosphere of 95% air and 5% $CO_2$.

After incubation the filter was removed from the chamber and non-migrated cells were scraped from the upper surface, and the filters washed with phosphate buffered saline three times. The filters were stained with Diff-Quik (Merz-Dade AG, Switzerland). The number of myocytes per 100×high power field that had migrated to the lower surface of the filters was determined microscopically. Six high power fields were counted per sample and the results were averaged.

Figure 2:
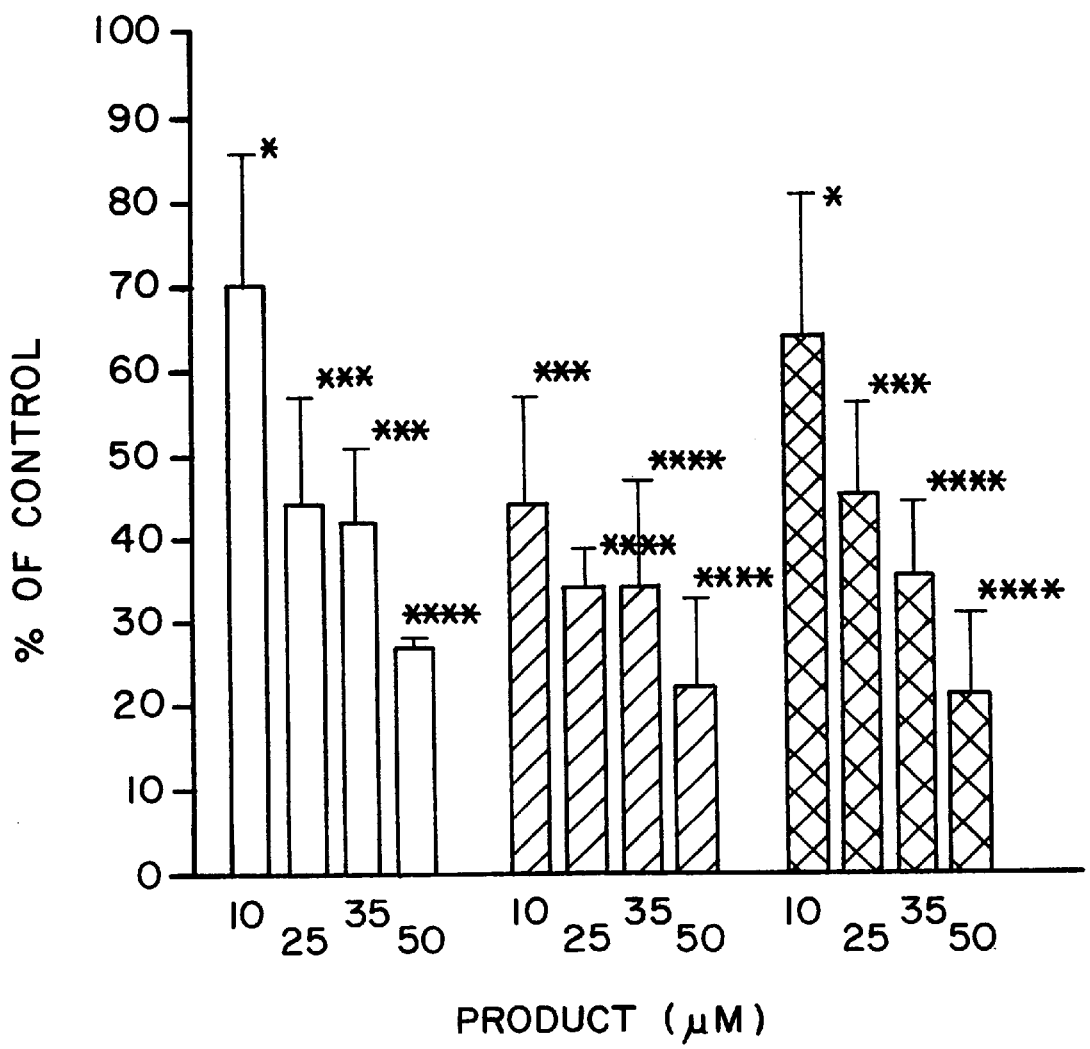
FIG. 2 is a graphical representation of the ability of lercanidipine and its enantiomers to interfere with the migration of arterial myocytes.

The results, expressed as migration of cells (as % of control) against amount of the compound of the invention (Lercanidipine and its enantiomers) tested, are shown in FIG. 2. These data demonstrate the ability of lercanidipine, and its enantiomers to interfere with the migration of arterial myocytes. All the tested compounds were able to inhibit myocytes migration in a dose-dependent manner with the (R)-enantiomer showing the most pronounced effect.

Example 6A
EFFECTS ON CHOLESTEROL METABOLISM IN MOUSE PERITONEAL MACROPHAGES

Atheromas contain two main cell types, macrophages and smooth muscle cells (R. Ross, Nature 362: 801 (1993)). Macrophages are derived from circulating monocytes and are the main lipid-loaded cells in the lesions. The mechanism by which they accumulate lipoprotein cholesterol and develop into foam cells depends mainly upon receptor-mediated processes, involving the so called "scavenger receptor" that recognizes chemically and biologically modified LDL, such as acetyl LDL (AcLDL) and oxidized LDL (Y. Kurihara et al., Curr. Opin. Lipidol 2: 295 (1991)). The scavenger receptor, unlike the LDL receptor, is not subject to feed-back regulation and the result is a massive accumulation of cholesterol in foam cells. Cholesterol accumulates in macrophages in esterified form by a process involving the enzyme acyl-coenzyme A-cholesterol acyltransferase (ACAT) which catalyzes the cholesterol esterification in cytoplasm (M. S. Brown et al., J. Biol. Chem. 255: 9344 (1980)). Only free cholesterol, i.e., unesterified cholesterol can be removed from macrophages.

Cholesterol esterification induced by AcLDL in mouse peritoneal macrophages was investigated as follows. Mouse peritoneal macrophages were obtained by peritoneal lavage from mice (Balb/c Charles River, Calco, Italy) three days after intraperitoneal injection of thioglycolate. Cells ($2 \times 3 \times 10^6$) were plated in 35 mm wells with Dulbecco's minimum essential medium containing 10% fetal bovine serum. After 3 hours, the dishes were washed to eliminate unattached cells and maintained in Dulbecco's minimum essential medium plus 10% fetal bovine serum for 24 hours before use. After cell plating, experiments were performed at 37° C. in serum free Dulbecco's minimum essential medium containing 0.2% essentially fatty acid-free bovine serum albumin, AcLDL, a specific ACAT inhibitor, S-58035 (See C. A. Ross et al., J. Biol, Chem. 259: 815–819 (1984)), and lercanidipine, or the lercanidipine enantiomers indicated. Human LDL (d=1.019–1.063 g/ml) were isolated from plasma of healthy volunteers by sequential ultracentrifugation (Beckman L5-50, Palo Alto, Calif.). For acetylation, LDL were dialyzed against 0. 15 M NaCl , pH 7.4, diluted with an equal volume of saturated sodium acetate and treated with acetic anhydride. For [$^{125}$I]AcLDL, lipoproteins were labelled with sodium [$^{125}$I]iodide desalted by gel filtration on Sephadex G-25 eluted with phosphate buffered saline. Specific activity was 100–200 cpm/ng of protein. Trichloroacetic acid non-precipitable radioactivity was below 2% of total. All lipoproteins were sterile filtered. The cells were incubated for 24 hours with the tested compounds. After substitution of the medium with fresh solution, incubation was continued for additional 24 hours. During this second incubation [$^{125}$I]AcLDL was added (50 $\mu$g/ml). Cholesterol esterification was measured after addition of [1-$^{14}$C] oleic acid (0.68 mCi sample) complexed with bovine serum albumin during the last 1 or 2 hours of incubation by subsequent determination of radioactivity associated with cellular cholesteryl esters.

Figure 3:
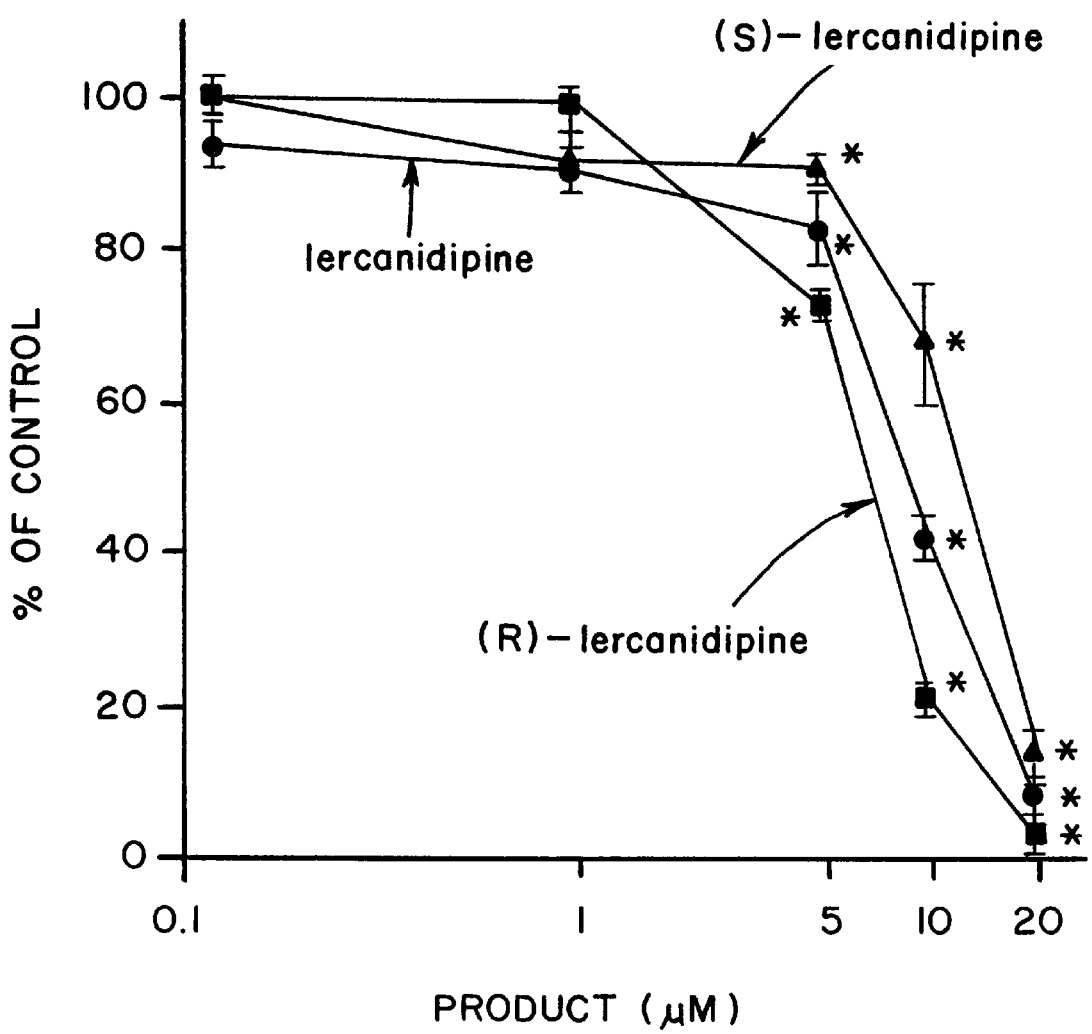
FIG. 3 is a graphical representation of the ability of lercanidipine and its enantiomers to inhibit the enzyme ACAT and cholesterol esterification induced by AcLDL in mouse peritoneal macrophage.

The results, expressed as level of inhibition (as % of control) against amount of the compound of the invention (Lercanidipine and its enantiomers) tested, are shown in FIG. 3. The compounds of the invention, particularly, lercanidipine and its enantiomers inhibited, in a concentration dependent manner, up to 90% of the formation of esterified cholesterol (in other words the compounds of the invention inhibited the esterifying effect of enzyme ACAT) induced by AcLDL in mouse peritoneal macrophage. The $IC_{50}$ values for lercanidipine and the enantiomers ranged from 8 to 15 $\mu$M, as shown in FIG. 3. The (R)-enantiomer was the most potent compound.

Example 6B
EFFECTS ON CHOLESTEROL METABOLISM IN MOUSE PERITONEAL MACROPHAGES

Another set of experiments was performed to evaluate the effect of lercanidipine on cholesterol esterification in macrophages loaded with cholesterol ester before the addition of the compounds of the invention, this condition being the same as in foam cells.

Cells, prepared according to the procedure in Example 6A, are loaded with cholesteryl esters by exposure for 24 hours to a medium containing 50 μg/ml acetyl LDL. ACAT inhibition was then determined as in Example 6A.

Figure 4:
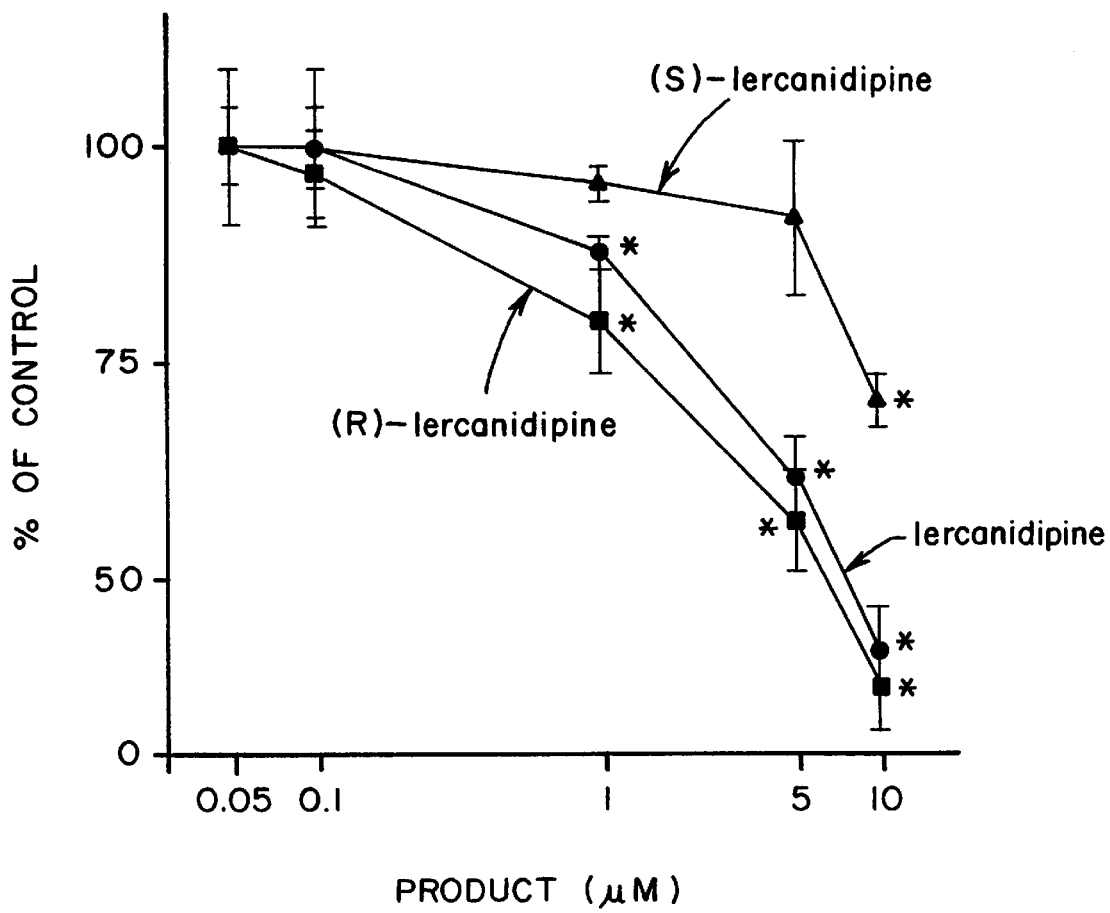
FIG. 4 is a graphical representation of the concentration-dependent effect of lercanidipine and its enantiomers on cholesterol esterification in cholesterol ester loaded macrophages.

The results, expressed as level of inhibition (as % of control) against amount of the compound of the invention (Lercanidipine and its enantiomers) tested, are shown in FIG. 4. The compounds of the invention, particularly, lercanidipine and its enantiomers inhibited, in a concentration dependent manner, up to 70% of the formation of esterified cholesterol induced by AcLDL in mouse peritoneal macrophage. The $IC_{50}$ value for the (R)-enantiomer was about 7 μM. The (R)-enantiomer of lercanidipine was slightly more potent than the racemate and (S)-lercanidipine was the least potent among the compounds tested.

Example 7
CHOLESTERYL ESTER HYDROLYSIS

It was shown that lercanidipine and its enantiomers at a 5 μM concentration did not impair the capability of the macrophages to hydrolyze the esterified cholesterol stored in the cytoplasm. These experiments were performed by incubating cells preloaded with [$^3$H]cholesterol in the presence of the specific ACAT inhibitor S-58035. The blockage of intracellular reesterification of cholesterol allowed the assessment of the ability of cells to hydrolyze the accumulated cholesterol esters.

For studies involving the quantitation of the hydrolysis of cholesteryl esters in cytoplasmic lipid droplets, cells, prepared according to the procedure in Example 6A, are loaded with cholesteryl esters by exposure for 24 hours to the medium containing 50 μg/ml acetyl LDL. [1,2-$^3$H] Cholesterol is included in all loading media at a concentration of 0.5 μCi/ml. After 24 hours loading period, during which time the radiolabeled cholesterol is incorporated and esterified, the cell monolayers are washed and incubated an additional 24 hours in medium containing 0.1% bovine serum albumin to allow the intracellular pools of labelled cholesterol to equilibrate to the same specific activity. To quantitate cholesteryl ester hydrolysis, the loaded cells are incubated for up to 24 hours in Dulbecco's minimum essential medium containing, 0.1% bovine serum albumin, lercanidipines, and the compound S-58035, an inhibitor of acyl-coenzyme A-cholesterol acyltransferase. The inhibition of acyl-coenzyme A-cholesterol acyltransferase prevents the reesterification of any free cholesterol generated by cholesteryl ester hydrolysis and thus allows assessment of the activity of the hydrolase. The hydrolysis of the cholesteryl esters is quantified by determining the decrease of radiolabeled cholesteryl esters (E. H. Harrison et al., *J. Lipid. Res.* 31: 2187 were washed with phosphate buffered saline and extracted with hexane:isopropanol (3:2 v/v). The media were extracted with chloroform:methanol (2:1 v/v). After solvent removal, free and esterified cholesterol were separated by TLC (isooctane:diethyl ether:acetic acid, 75:25:2 by volume). Cholesterol mass or radioactivity of the spots were determined by an enzymatic method (Boehringer Mannheim, Germany) (F. Bernini et al.,*Atherosclerosis* 104: 19 (1993)) or by liquid scintillation counting (Lipoluma Lumac, Landgraf, The Netherlands) respectively.

The results are given in Table 2. These data show that the addition of lercanidipine and its enantiomers did not influence the cellular hydrolytic activity, documented by the values of radioactivity in the esterified cholesterol fraction. The compounds of the invention do not impair the capability of the macrophages to hydrolyze the esterified cholesterol stored in the cytoplasm.

TABLE 2

EFFECT OF LERCANIDIPINE AND ITS ENANTIOMERS ON CHOLESTERYL ESTER HYDROLYSIS IN MACROPHAGES

| | % of cholesteryl ester |
|---|---|
| AcLDL 50 μg/ml | 31 ± 0.8 |
| AcLDL 50 μg/ml + S-58035 1 μg/ml | 15 ± 0.5 |
| AcLDL 50 μg/ml + S-58035 1 μg/ml + 5 × 10$^{-6}$M LE* | 12 ± 1.2 |
| AcLDL 50 μg/ml + S-58035 1 μg/ml + 5 × 10$^{-6}$M (S)-LE* | 14 ± 0.4 |
| AcLDL 50 μg/ml + S-58035 1 μg/ml + 5 × 10$^{-6}$M (R)-LE* | 16 ± 2.1 |

*LE = lercanidipine

Example 8
EFFECTS OF LERCANIDIPINE ON CHEMICAL OXIDATION OF LDL

Experimental reports ascribe a key role for the oxidative modification of LDL in the early stages of atherosclerosis in humans. These reports suggest that LDL undergoes oxidative modifications in vivo (D. Steinberg et al., *N. Eng. J. Med.* 320: 915 (1989); D. Steinberg et al.,*JAMA* 264: 3047 (1990); D. Steinberg, *Circulation* 84: 1420 (1991); S. Yla-Herttuala, *Ann. Med.* 23: 561 (1991); U. P. Steinbrecher, *Curr. Opin. Lipidol.* 1: 411 (1990); J. L. Witztum, *Lancet* 344: 793 (1994)) and that oxidatively modified LDL (OX-LDL) may induce atherogenesis by a number of mechanisms, including its enhanced uptake in tissue macrophages (via the scavenger receptor pathway) which leads to lipid accumulation, and chemotactic activity for monocytes, and cytotoxicity to arterial wall endothelial cells (S. Parthasarathy et al., *Prog. Lipid. Res.* 31: 127 (1992).

The ability of Lercanidipine to function as an antioxidant was evaluated by incubating LDL, isolated from human plasma, for 22 hours with an oxidizing agent (20 μM Cu++) in the presence of different concentrations of the test compounds (0.01 μM–50 μM). The LDL oxidation was followed by monitoring conjugated diene formation with a ultraviolet (UV) spectrometer at 234 nm.

The experimental conditions were as follows. LDL (d=1.019–1.063) were isolated from human pooled plasma by sequential ultracentrifugation at 4° C. and 40,000 rpm in a 50 Ti rotor, using a L5-50 ultracentrifuge (Beckman, Palo Alto, Calif.). The LDL were then dialyzed against 0.15 M NaCl containing 0.01% ethylenediaminetetraacetic acid pH 7.4, sterilized by filtration through a 0.2 μM millipore filter and stored at 4° C. under nitrogen in the dark until use (up to 3 weeks). Before use, LDL were dialyzed against ethylenediaminetetraacetic acid free phosphate buffered saline, pH 7.4, on Sephadex G-25 columns (PD-10, Pharmacia Fine Chemicals, Uppsala, Sweden). Then the LDL were filtered through a sterile 0.22 μM filter. In a phosphate buffered saline (50 μg lipoprotein protein/ml), the LDL were oxidized by incubation at 25° C. with 20 μM $CuSO_4$ for 3 hours. The lercanidipine solution was prepared as a 10$^{-2}$ M stock solution in methanol or ethanol and added as a methanol or ethanol solution (maximum 1% v/v) prior to addition of the copper solution. The effect of lercanidipine on the oxidation of LDL was determined by continuous monitoring of the formation of conjugated dienes by recording the increase in the absorbance at 234 nm at 5 min intervals during a three hour period, against a phosphate buffered saline blank, using a UV spectrophotometer (Beckman DU 640) equipped with a continuous reading and an automatic 6-cell changer. The time prior to the onset of oxidation (lag time) was calculated as the intercept between the line of the maximum slope of the propagation phase and the x-axis. The results are shown in Table 3.

TABLE 3

EFFECT OF LERCANIDIPINE ON THE LAG TIME OF LDL OXIDATION

| Lercanidipine μM | Lag time |
| --- | --- |
| 0.0 | 46.5 ± 4.6 |
| 0.5 | 45.2 ± 3.7 |
| 1.0 | 49.8 ± 4.7 |
| 2.5 | 53.6 ± 3.3* |
| 5.0 | 73.2 ± 4.8** |
| 10.0 | 112.7 ± 5.2** |

*$P < 0.05$
**$P < 0.01$

As shown in Table 3, lercanidipine, at a concentration of 10 μM clearly increased the lag time for LDL oxidation, the time required before oxidation begins, more than 2 times. The data show that the effect of the racemate was concentration-dependent, with concentrations greater than or equal to 2.5 μM significantly suppressing the onset of LDL oxidation. The activity of the resolved enantiomers was comparable to that of the racemate.

Example 9A
EFFECTS OF LERCANIDIPINE ON CELL-MEDIATED OXIDATION

The antioxidant capacity of the compounds of the invention, on cell-mediated oxidation, was evaluated by incubating LDL and mouse monocyte-macrophage cells (ATCC TIB 67 J774A.1) with $CuSO_4$ solution in the presence of apolipoprotein B (Apo B), lercanidipine or one of its enantiomers at several concentrations. The inhibition of formation of aldehydic breakdown products, i.e., secondary metabolites of lipid peroxidation, malonic dialdehyde (MDA), was assessed by detection of dialdehyde formation using the thiobarbituric acid assay (A. N. Hanna et al., Biochem. Pharmacol. 45: 753 (1993)).

The antioxidant capacity was evaluated by incubating ethylene-diaminetetraacetic acid free-LDL under sterile conditions with 5 μM Cu++ (100 μg Apo B/ml) in the presence of J774A.1 cells. Oxidation was stopped after 22 hours incubation by addition of butylated hydroxytoluene to the medium (final concentration 40 μM) dissolved in ethanol. To the incubated sample (0.250 ml), was added trichloroacetic acid (0.750 ml, 0.20% w/v) followed by of thiobarbituric acid (0.750 ml, 0.67% w/v). The samples were heated at 100° C. for 20 min, followed by cooling and centrifugation. Malonic dialdehyde equivalents were calculated using 1,1,3,3-tetramethoxypropane as the standard.

Figure 5:
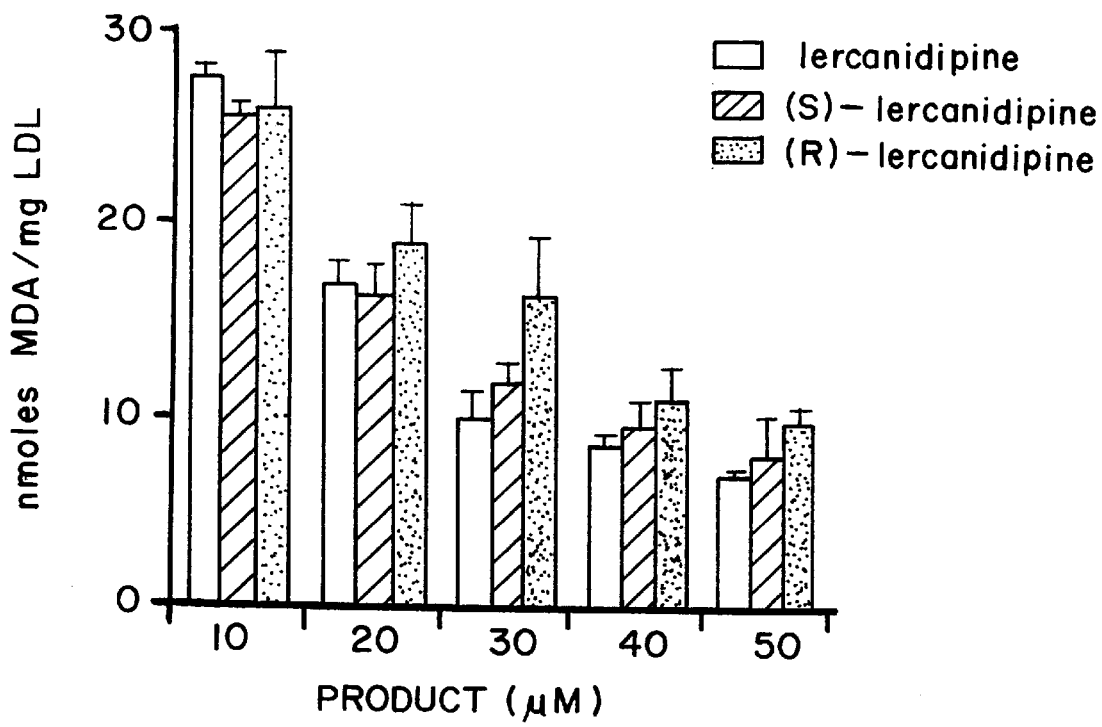
FIGS. 5 and 6 are graphical representations of the effect of lercanidipine and its enantiomers on cell-mediated oxidation of LDL.

The results, expressed as nanomoles of MDA produced against amount of the compound of the invention (Lercanidipine and its enantiomers) tested, are shown in FIG. 5. The results show that lercanidipine and its enantiomers were effective in reducing LDL oxidation.

Example 9B
EFFECTS OF LERCANIDIPINE ON CELL-MEDIATED OXIDATION

Following the procedure in Example 9A, the effects of lercanidipine on cell-mediated oxidation were studied with a different cell line which shares many of the properties of endothelial cells (EAhy-926). (The cells were provided by: Prof. A. Catapano, Pharmacology Dept., Universita Statale—Milano.) (These or other endothelial cells can be obtained as described by C-J. S. Edgall et al., Proc. Nat. AcAd. Sci., 80: 3734–3737, (1983); and Gimbrone, M., Prog. Hemostasis Thromb., 3: 1–28, (1976)). The cells were treated with lercanidipine at a concentration of from about 10 to about 100 μM.

Figure 6:
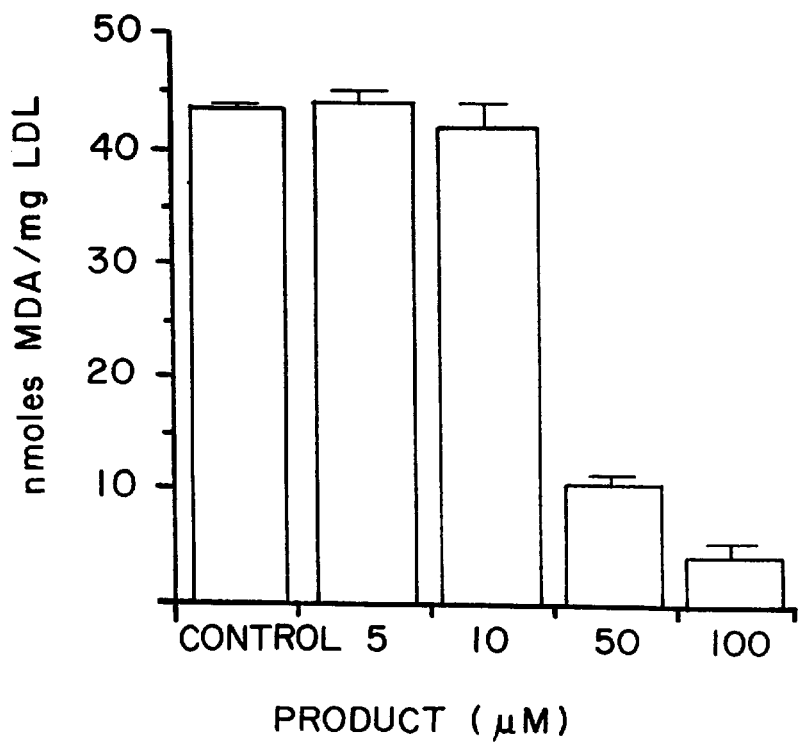

The results, expressed as nanomoles of MDA produced against amount of Lercanidipine, are shown in FIG. 6. The results show that lercanidipine reduced the oxidation of LDL at a concentration of 10 to 100 μM.

Example 9C
EFFECTS OF LERCANIDIPINE ON CELL-MEDIATED OXIDATION

In experiments 9A and 9B, the cell-mediated oxidation effects of lercanidipine were investigated after incubation for 22 hours. In order to investigate the lower potency shown by lercanidipine in these conditions, the extent of lipid peroxidation in its presence was studied over time. A reaction mixture was prepared according to the procedure in Example 9A, using lercanidipine at a concentration of 30 μM. Samples were withdrawn from the incubation medium and the oxidation product, MDA, measured as described above.

Figure 7:
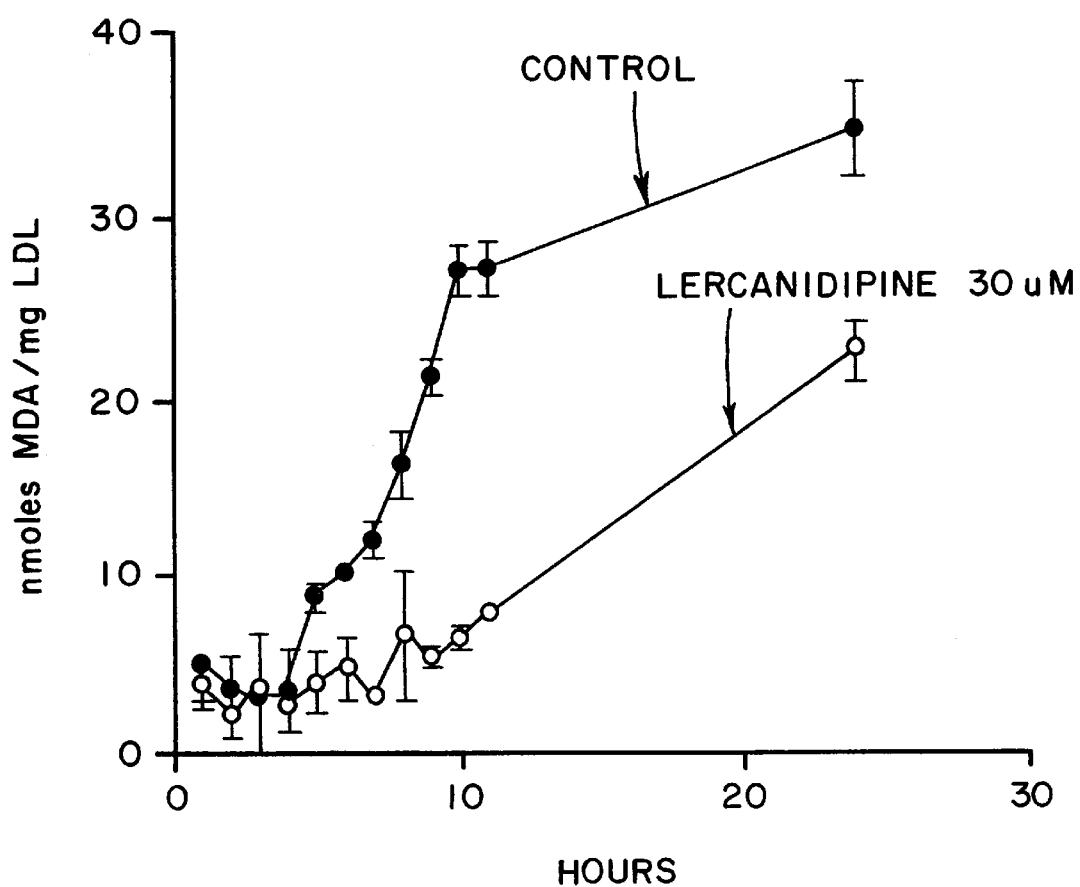
FIG. 7 is a time course plot of cell-mediated oxidation and the effects of lercanidipine after incubation.

The results, expressed as nanomoles of MDA produced against time are shown in FIG. 7. It can be seen that at a concentration of 30 μM, lercanidipine exerted a very high inhibition of lipid oxidation after 10 hours incubation. This shows that lercanidipine, administered at an appropriate time is as effective on cell mediated LDL oxidation as it is on Cu++-mediated oxidation.

Lercanidipine proved the most potent 1,4-dihydropyridine tested in the assays herein, its potency being one order of magnitude higher than that of lacidipine, the most potent of the 1,4-dihydropyridine compounds previously known to have this activity.

Example 10
EFFECTS ON BLOOD PRESSURE IN HYPERTENSIVE DOGS

The antihypertensive effects of oral administration of lercanidipine and its enantiomers were tested in renal hypertensive dogs.

Male Beagle dogs weighing 12–13 kg, aging 1–3 years (Nossan Allevamenti, Italy) were used. Chronic sustained hypertension was induced by bilateral renal artery constriction, according to the Goldblatt method "two-kidney, two clip hypertension". Under barbiturate anaesthesia (35 mg/kg i.v.), during two different surgical interventions one month apart from each other, both renal arteries were clipped with original renal silver clips and narrowed by about 60–70%. After two months from the last intervention, an experimental renal hypertension was produced and the animals were suitable for the implantation of a catheter. Under sodium pentobarbital anaesthesia (35 mg/kg i.v.), in sterile conditions, the dogs were catheterized by inserting an indwelling cannula (PE 200 Clay Adams) into the ascending aorta through the right common carotid artery. The catheter was subcutaneously exteriorized at the back of the neck, filled with heparinized saline solution and flushed daily to prevent clotting. After a week recovery time from surgery, the animals were connected to a HP 1290A pressure transducer connected to an HP 8805B carrier amplifier of a Hewlett Packard HP 7700 multichannel polygraph, to monitor the arterial blood pressure. Heart rate was manually computed from the pressure trace.

All animals were alternatively treated with placebo, lercanidipine and its (R)- and (S)- enantiomers. The drugs were administered orally with a straight round aseptic tip catheter (Pores Serlat—France). The drugs were suspended in aqueous 0.5% Methocel A4C plus Antifoam M10 (10%). The amount administered was 1 ml/kg.

The suspending medicine was used as placebo. During experimental performance, the arterial blood pressure was continuously recorded 30 min. before (basal values) and up to 8 hours after drug administration.

Lercanidipine and (S)-lercanidipine induced a dose-related decrease in arterial blood pressure. The $ED_{25}$ values (dose inducing 25% decrease in DBP at peak effect) were evaluated by linear regression analysis and summarized in the Table 4.

TABLE 4

| Compound | $ED_{25}$ (mg/kg) 95% C.L. |
|---|---|
| Lercanidipine | 0.9 (0.5 ÷ 1.6) |
| (S)-Lercanidipine | 0.4 (0.3 ÷ 0.7) |
| (R)-Lercanidipine | >>30 |

C.L. = Confidence limits

The (S)-Lercanidipine enantiomer exerted the most potent antihypertensive action. This compound was two fold more efficacious at lowering blood pressure than the racemate. The (R)-enantiomer did not affect blood pressure up to 30 mg/kg (<10% decrease in DBP).

Example 11A
HIGH TEMPERATURE STRESS STABILITY

Lercanidipine hydrochloride hemihydrate, prepared according to the procedure described in U.S. Pat. No. 4,705,797, was compared with anhydrous lercanidipine prepared according to Example 3, to determine the stress stability of the compounds. The two samples, lercanidipine hydrochloride hemihydrate, and anhydrous lercanidipine hydrochloride were heated, in the light, at 100° C. for 48 hours. The samples were tested at the following times; 0 hours, 24 hours, and 48 hours. The purity of the lercanidipine was checked by HPLC analysis under the following conditions:

Column: m-Bondapak C-18 (Waters), particle size 10 mm, 300×3.9 mm i.d.

Eluant: $CH_3CN$ (61%): 0.15M $NaClO_4$ aqueous solution at pH 3 (adjusted with $HClO_4$) (39%; v/v)

Elution: isocratic

Flow: 1.5 mL/min

Temp. 25° C.

Detector: UV (240 nm)

Attenuation: 0.05 AUFS

The results, expressed as assay % of the compound present, based on an HPLC analysis, are shown in Table 5 below:

TABLE 5

Stress Stability at 100° C.

| | Assay % by HPLC | | |
|---|---|---|---|
| Compound | 0 hr | 24 hrs | 48 hrs |
| Anhydrous | 99.74 | 99.36 | 99.01 |
| Hemihydrate | 99.85 | 92.35 | 90.96 |

From Table 5, it can be seen that the anhydrous form of lercanidipine hydrochloride exhibited superior stability over the hydrated form.

Example 11 B
WATER CONTENT AT 75% RELATIVE HUMIDITY

Samples of anhydrous lercanidipine hydrochloride and lercanidipine hydrochloride hemihydrate were placed in open polyethylene bags in flasks and heated, in the dark, at 60° C. and 75% relative humidity. The samples were checked for hygroscopicity by determination of the water content using the Karl-Fisher method. The samples were tested at 8 and 15 days.

Two additional samples of the anhydrous lercanidipine hydrochloride and lercanidipine hydrochloride hemihydrate were placed in open polyethylene bags in flasks and heated, in the dark, at 40° C. and 75% relative humidity. The samples were tested as described above at 8 and 15 days. The results of these tests are shown in Table 6.

TABLE 6

Water Content at 75% Relative Humidity

| | | Water Content | | |
|---|---|---|---|---|
| | | 0 days | 8 days | 15 days |
| 60° C. | Anhydrous | 0.28 | 0.85 | 0.77 |
| | Hemihydrate | 1.42 | 4.00 | 4.04 |
| 40° C. | Anhydrous | 0.28 | 0.30 | 0.32 |
| | Hemihydrate | 1.42 | 3.14 | 3.05 |

From Table 6, it can be seen that the anhydrous lercanidipine has a much lower tendency to absorb water than the hemihydrate form. The lack of hygroscopicity is advantageous because the anhydrous compound will remain unchanged. Thus, it will be easier to handle during the preparation and dispensing of pharmaceutical formulations.

The invention has been described above by reference to preferred embodiments but, as those skilled in the art will appreciate, many additions, omissions and modifications are possible all within the scope of the claims below.

We claim:

1. A method for preparing anhydrous methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate hydrochloride, which comprises (a) reacting 2,6-dimethyl-5-methoxycarbonyl-4-(3-nitrophenyl)-1,4-dihydropyridine-3-carboxylic acid with a halogenating agent in an aprotic solvent to produce 2,6-dimethyl-5-methoxycarbonyl-4-(3-nitrophenyl)-1,4-dihydropyridine-3-carboxylic acid chloride;

(b) reacting said 2,6-dimethyl-5-methoxycarbonyl-4-(3-nitrophenyl)-1,4-dihydropyridine-3-carboxylic acid chloride with 2,N-dimethyl-N-(3,3-diphenylpropyl)-1-amino-2-propanol in an aprotic solvent;

(c) isolating the resultant hydrochloride compound; and (d) recrystallizing said hydrochloride compound in two successive steps, regardless of sequence, from a solution of said compound in;
   i) an aprotic solvent; and
   ii) a protic solvent;

thereby isolating methyl 1,1, N-trimethyl-N-(3,3-diphenylpropyl)-2-aminoethyl 1,4-dihydro-2,6-dimethyl-4-(3-nitrophenyl)-pyridine-3,5-dicarboxylate as its anhydrous hydrochloride.

2. The method according to claim 1, wherein with a halogenating agent selected from the group consisting of thionyl chloride, phosphorus pentachloride, phosphorus trichloride, phosphorus oxychloride and oxalyl chloride.

3. The method according to claim 1, wherein the aprotic solvent for said step (a) is chloroform, dichloromethane, dichloroethane, chlorobenzene, 1,1,1-trichloroethane, ethyl acetate, methyl acetate, tetrahydrofuran, dioxane, dimethylformamide, dimethylcarbonate or any mixture thereof.

4. The method according to claim 1, wherein the aprotic solvent for said step (b) is a chlorinated or non-chlorinated solvent selected from the group consisting of chloroform, dichloromethane, dichloroethane, chlorobenzene, 1,1,1-trichloroethane, ethyl acetate, methyl acetate, tetrahydrofuran, dioxane, N,N-dimethylformamide, dimethylcarbonate, toluene, xylene, an ($C_5$–$C_7$) alkane, a ($C_5$–$C_7$) cycloalkane and mixtures thereof.

5. The method according to claim 1 wherein the recrystallization of said compound in said aprotic solvent precedes the recrystallization of said compound in said protic solvent.

6. A method according to claim 5 wherein the aprotic crystallization solvent is ethyl acetate, methyl acetate or acetone.

7. The method according to claim 5 wherein the protic crystallization solvent is selected from the group consisting of methanol, ethanol, n-propanol, i-propanol, n-butanol, s-butanol, t-butanol and mixtures thereof, optionally in a mixture with water.

8. The method of claim 3, wherein said aprotic solvent for said halogenating step (a) is ethyl acetate.

9. The method according to claim 1, wherein the compound methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate hydrochloride has a two degree melting point within the range of 185° C. to 190° C.

* * * * *